US012691061B1

(12) United States Patent
Hanlon

(10) Patent No.: US 12,691,061 B1
(45) Date of Patent: Jul. 28, 2026

(54) CAFFEINE-FREE READY-TO-DRINK COMPOSITION FOR PRE-CAFFEINE COGNITIVE PRIMING

(71) Applicant: Michael Hanlon, Canonsburg, PA (US)

(72) Inventor: Michael Hanlon, Canonsburg, PA (US)

( * ) Notice: Subject to any disclaimer, the term of this patent is extended or adjusted under 35 U.S.C. 154(b) by 0 days.

(21) Appl. No.: 19/447,145

(22) Filed: Jan. 13, 2026

(51) Int. Cl.
| | |
|---|---|
| *A61K 9/00* | (2006.01) |
| *A23L 2/54* | (2006.01) |
| *A23L 2/56* | (2006.01) |
| *A23L 2/68* | (2006.01) |
| *A23L 27/00* | (2016.01) |
| *A23L 27/40* | (2016.01) |
| *A61K 31/198* | (2006.01) |
| *A61K 31/4415* | (2006.01) |
| *A61K 31/4525* | (2006.01) |
| *A61K 31/7068* | (2006.01) |
| *A61K 31/714* | (2006.01) |
| *A61K 33/06* | (2006.01) |
| *A61K 47/12* | (2006.01) |
| *A61K 47/24* | (2006.01) |

(Continued)

(52) U.S. Cl.
CPC .............. *A61K 9/0095* (2013.01); *A23L 2/54* (2013.01); *A23L 2/56* (2013.01); *A23L 2/68* (2013.01); *A23L 27/40* (2016.08); *A23L 27/84* (2016.08); *A23L 27/88* (2016.08); *A61K 9/0053* (2013.01); *A61K 31/198* (2013.01); *A61K 31/4415* (2013.01); *A61K 31/4525* (2013.01); *A61K 31/7068* (2013.01); *A61K 31/714* (2013.01); *A61K 33/06* (2013.01); *A61K 47/12* (2013.01); *A61K 47/24* (2013.01);

*A61K 47/36* (2013.01); *A61K 47/40* (2013.01); *B65D 65/463* (2013.01); *B65D 75/26* (2013.01); *B65D 75/36* (2013.01); *B65D 81/267* (2013.01)

(58) Field of Classification Search
None
See application file for complete search history.

(56) References Cited

U.S. PATENT DOCUMENTS

| | | | |
|---|---|---|---|
| 8,993,033 B2 * | 3/2015 | Bhargava | A23L 33/105 |
| | | | 426/74 |
| 2009/0105331 A1 * | 4/2009 | Schaffner | A23L 29/20 |
| | | | 514/777 |

(Continued)

*Primary Examiner* — Dominic Lazaro
(74) *Attorney, Agent, or Firm* — The Rapacke Law Group, P.A.

(57) ABSTRACT

A caffeine-free, ready-to-drink liquid composition is provided for pre-caffeine cognitive priming. A unit dose of about 2.0 to 3.0 ounces at pH about 3.0 to 3.5 comprises N-acetyl L-tyrosine, citicoline, phosphatidylserine, one or more adaptogenic botanicals, L-citrulline, piperine, vitamins B6 and B12, a magnesium source, and an acidulant system including malic acid with limited citric acid. A sensory agent, such as ginger $CO_2$ extract, yields perceivable warming or tingling within minutes, with palate clearance in about sixty seconds. Methods include administering the composition about 2 to 45 minutes before consuming a caffeinated beverage to provide rapid, predictable onset while maintaining beverage flavor compatibility. Packaged systems may use nitrogen-flushed PET or glass, cold-fill, and high-pressure processing or low-temperature pasteurization, with optional low-level carbonation and microencapsulation to manage bitterness, dissolution, and stability.

18 Claims, 3 Drawing Sheets

(51) Int. Cl.

| | |
|---|---|
| *A61K 47/36* | (2006.01) |
| *A61K 47/40* | (2006.01) |
| *B65D 65/46* | (2006.01) |
| *B65D 75/26* | (2006.01) |
| *B65D 75/36* | (2006.01) |
| *B65D 81/26* | (2006.01) |

(56)                     References Cited

U.S. PATENT DOCUMENTS

2009/0162483  A1*   6/2009   Constantine  ............. A23L 2/56
                                                              426/62
2012/0100257  A1*   4/2012   Lambach  ................ A23L 33/40
                                                              426/546
2021/0227855  A1*   7/2021   Wan  .......................... A23F 3/30

* cited by examiner

ADMINISTRATION TIMING TIMELINE 100:

102 — TO: INGEST UNIT DOSE

104 — T+1–10 MIN: PERCEIVABLE TINGLING OR WARMTH

106 — T+2–25 MIN: COGNITIVE PRIMING WINDOW

108 — T+10–30 MIN: CONSUME CAFFEINATED BEVERAGE

110 — PALATE CLEARANCE BY ABOUT 60 SECONDS AFTER SWALLOW

Figure 2:
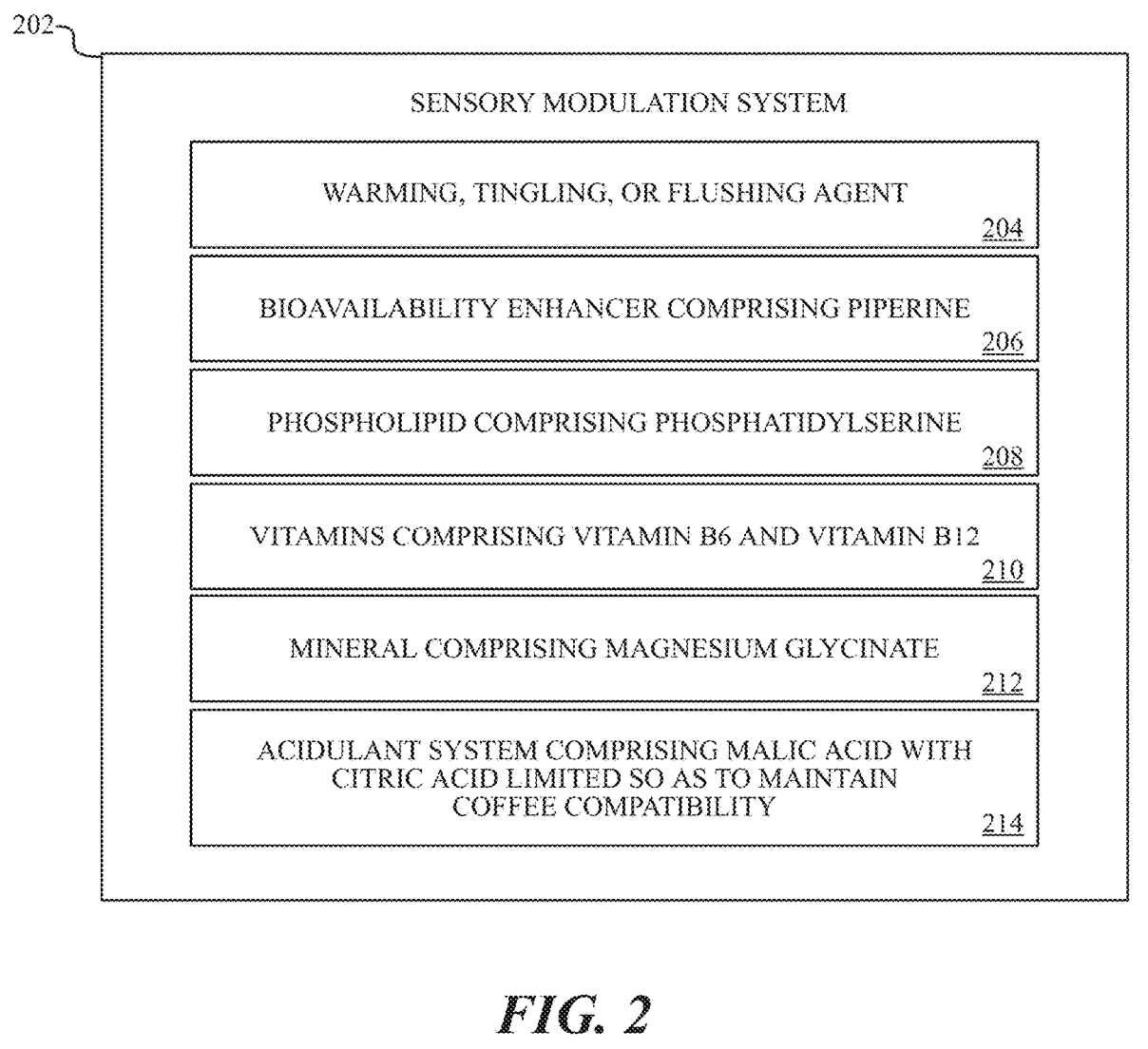

202

SENSORY MODULATION SYSTEM

WARMING, TINGLING, OR FLUSHING AGENT

204

BIOAVAILABILITY ENHANCER COMPRISING PIPERINE

206

PHOSPHOLIPID COMPRISING PHOSPHATIDYLSERINE

208

VITAMINS COMPRISING VITAMIN B6 AND VITAMIN B12

210

MINERAL COMPRISING MAGNESIUM GLYCINATE

212

ACIDULANT SYSTEM COMPRISING MALIC ACID WITH
CITRIC ACID LIMITED SO AS TO MAINTAIN
COFFEE COMPATIBILITY

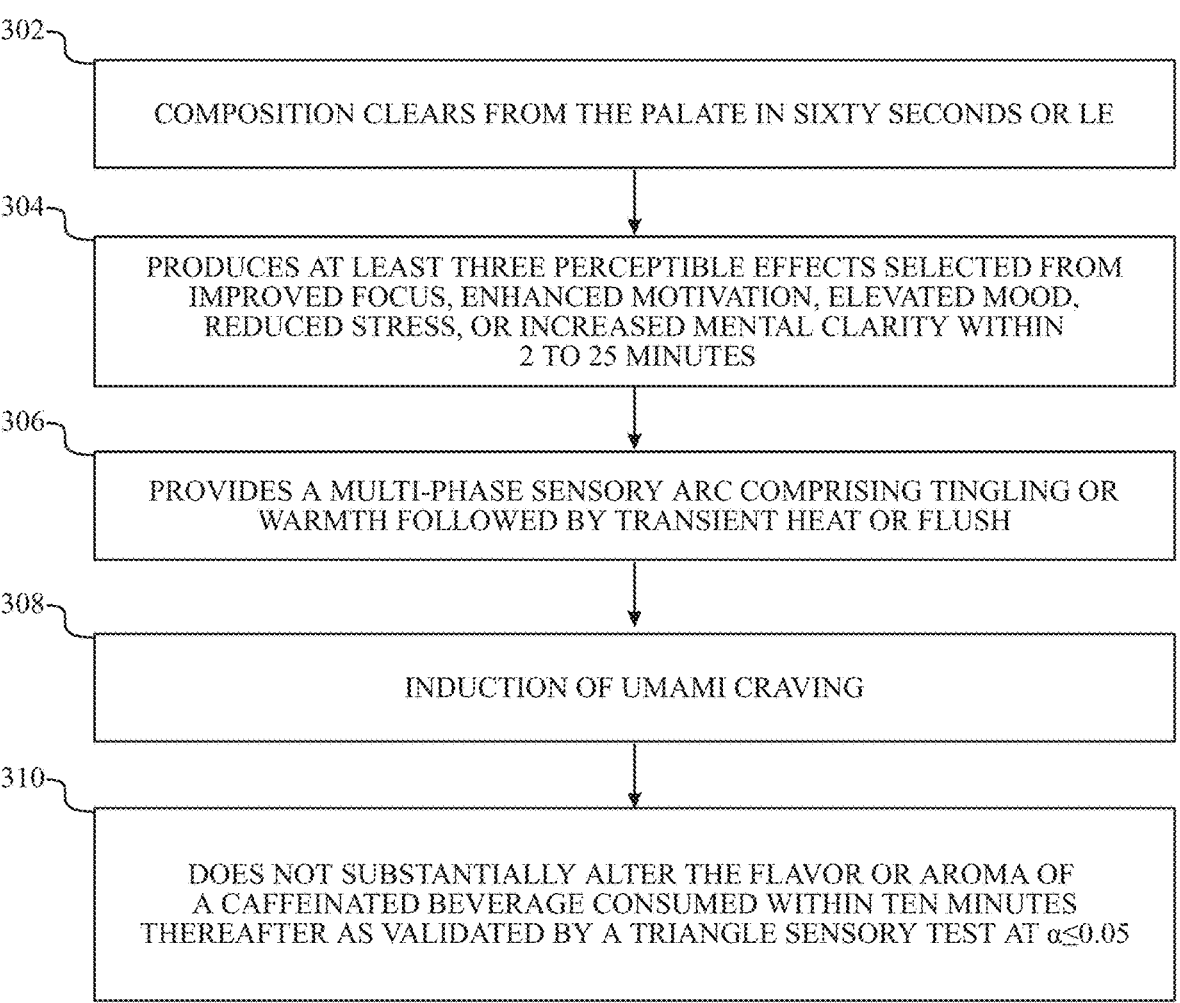

PRE-CAFFEINE COGNITIVE PRIMING FLOWCHART 300:

302 — COMPOSITION CLEARS FROM THE PALATE IN SIXTY SECONDS OR LE

304 — PRODUCES AT LEAST THREE PERCEPTIBLE EFFECTS SELECTED FROM IMPROVED FOCUS, ENHANCED MOTIVATION, ELEVATED MOOD, REDUCED STRESS, OR INCREASED MENTAL CLARITY WITHIN 2 TO 25 MINUTES

306 — PROVIDES A MULTI-PHASE SENSORY ARC COMPRISING TINGLING OR WARMTH FOLLOWED BY TRANSIENT HEAT OR FLUSH

308 — INDUCTION OF UMAMI CRAVING

310 — DOES NOT SUBSTANTIALLY ALTER THE FLAVOR OR AROMA OF A CAFFEINATED BEVERAGE CONSUMED WITHIN TEN MINUTES THEREAFTER AS VALIDATED BY A TRIANGLE SENSORY TEST AT $\alpha \leq 0.05$

*FIG. 3*

CAFFEINE-FREE READY-TO-DRINK COMPOSITION FOR PRE-CAFFEINE COGNITIVE PRIMING

TECHNICAL FIELD

The embodiments generally relate to the technical field of nutraceutical compositions for cognitive enhancement.

BACKGROUND

Conventional products for cognitive enhancement often rely on stimulants to promote alertness and focus. Caffeinated beverages such as coffee, tea, and energy drinks act primarily as adenosine receptor antagonists and are widely used for rapid increases in perceived wakefulness. Formulators frequently include sugars or non nutritive sweeteners, flavorings, and acids to create familiar taste profiles suitable for routine consumption. Users typically ingest these products on an as needed basis, and onset depends on gastric emptying, dose, and individual tolerance.

Other products position themselves as nootropic blends that combine vitamins, amino acids, choline donors, botanical extracts, or minerals. These products aim to support neurotransmitter synthesis, cellular energy production, or stress resilience. Common delivery formats include ready to drink shots, powders for reconstitution, capsules, tablets, and chewables. Manufacturers design these formats to balance solubility, stability, and sensory attributes while targeting convenient, portable use.

Some conventional systems emphasize vascular or metabolic support through ingredients associated with nitric oxide pathways or mitochondrial function. These systems seek to influence subjective energy and mental stamina without increasing stimulant load. Producers may use encapsulation, acidity control, or specific processing steps to preserve ingredient potency over shelf life and to manage flavor carryover when products are taken in proximity to other beverages.

Users employ conventional products before, during, or after cognitively demanding tasks based on personal routines. Although these products can provide benefits, users may experience variability in onset timing, intensity, and duration. Taste compatibility with other beverages can vary, and certain formulations can linger on the palate longer than desired. Some products rely on sensory cues such as warming or tingling to signal activation, while others provide limited immediate feedback. Packaging and processing choices seek to maintain stability, yet they can influence mouthfeel, carbonation levels, and overall flavor perception.

SUMMARY

This summary is provided to introduce a variety of concepts in a simplified form that is further disclosed in the detailed description of the embodiments. This summary is not intended to identify key or essential inventive concepts of the claimed subject matter, nor is it intended to determine the scope of the claimed subject matter.

The disclosed compositions, methods, and systems provide a caffeine-free, pre-caffeine cognitive priming approach designed for rapid, predictable onset and compatibility with subsequent caffeinated beverages. In one aspect, a unit-dose liquid composition of about 2.0 to 3.0 ounces at a controlled pH includes a defined combination of actives, such as a dopamine precursor, a choline donor, adaptogenic botanicals, a nitric-oxide or mitochondrial enhancer, phospholipids, vitamins, minerals, and a bioavailability enhancer. A sensory modulation component produces warming, tingling, or related cues that signal initiation. The formulation clears from the palate within about sixty seconds and maintains coffee compatibility, including when a user consumes a caffeinated beverage shortly thereafter. These features address variability in onset and flavor carryover often encountered with conventional products by providing perceptible effects within a defined window and by minimizing lingering taste.

In another aspect, a method administers the composition minutes before a caffeinated beverage to prime dopaminergic and cholinergic pathways and to synergize with later caffeine consumption without requiring an increased caffeine dose. The approach delivers at least three perceivable outcomes, such as improved focus or clarity, within a target time window in a majority of users, while a multi-phase sensory arc offers immediate feedback that the composition is active. By timing administration before caffeine, users can structure routines around predictable onset and intensity rather than relying on stimulant load alone.

In a further aspect, a packaged system supplies the composition with clear use instructions and employs processing and packaging conditions, such as nitrogen-flushed containers, cold-fill, and high-pressure processing or low-temperature pasteurization, to protect potency and deliver stable shelf life. Optional low-level carbonation and selective microencapsulation can refine mouthfeel, reduce bitterness, and support rapid dissolution, thereby improving sensory acceptance without compromising efficacy. Collectively, these elements offer portable dosing, rapid palate clearance, immediate sensory confirmation, beverage compatibility, and manufacturing stability, addressing functional shortcomings commonly associated with conventional stimulant-centric or nootropic products.

Other illustrative variations within the scope of the invention will become apparent from the detailed description provided hereinafter. The detailed description and enumerated variations, while disclosing optional variations, are intended for purposes of illustration only and are not intended to limit the scope of the invention.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein:

FIG. 2 illustrates a composition schematic identifying representative constituents of a caffeine-free, ready-to-drink liquid composition, according to some embodiments; and FIG. 3 illustrates a pre-caffeine cognitive priming flowchart that summarizes representative functional characteristics of a caffeine-free, ready-to-drink liquid composition, according to some embodiments.

DETAILED DESCRIPTION

Figure 1:
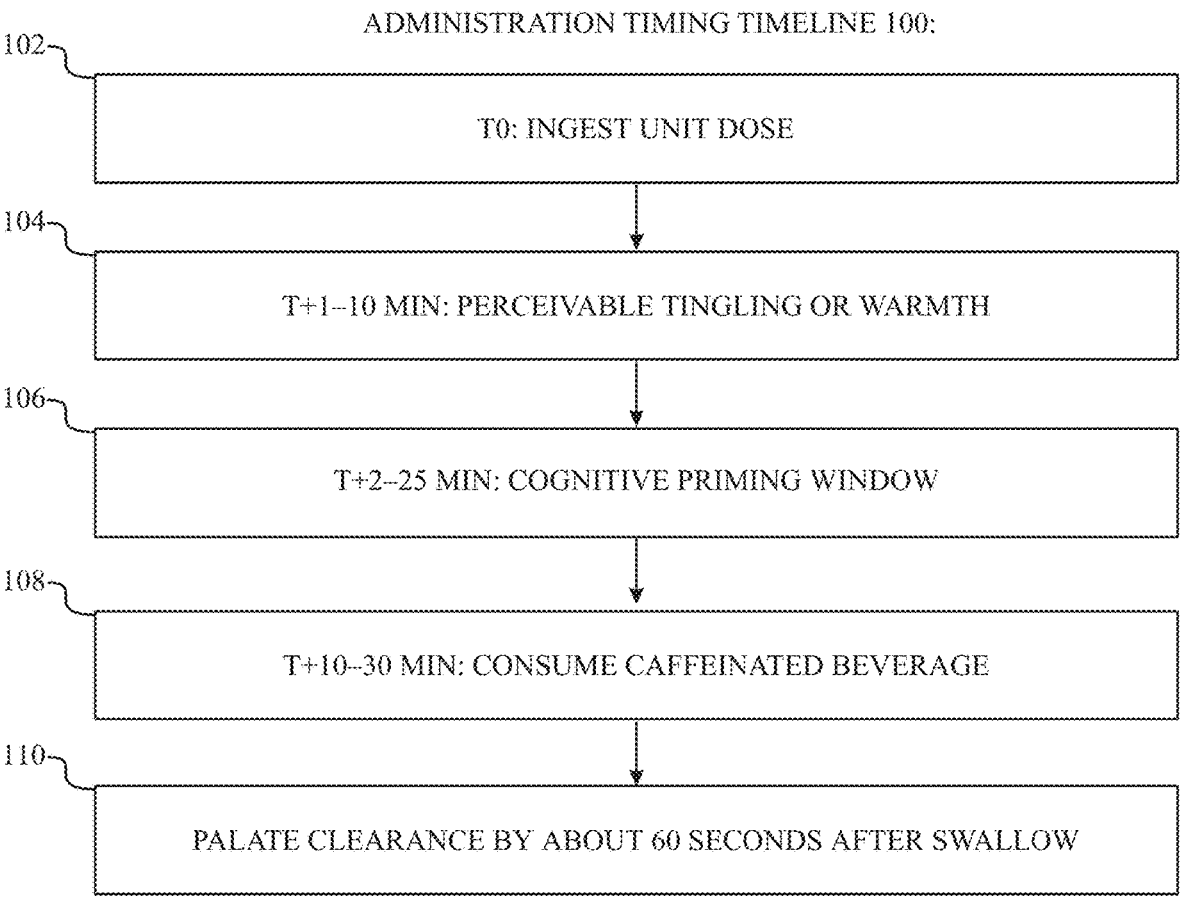
FIG. 1 illustrates an administration timing timeline for a single unit dose of a caffeine-free, ready-to-drink liquid composition, according to some embodiments.

The specific details of the single embodiment or variety of embodiments described herein are set forth in this application. Any specific details of the embodiments described herein are used for demonstration purposes only, and no unnecessary limitation(s) or inference(s) are to be understood or imputed therefrom.

Before describing exemplary embodiments in detail, it is noted that the embodiments reside primarily in combinations of components related to devices and systems. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

A representative composition may include a dopamine precursor, a choline donor, adaptogenic botanicals, a vascular or mitochondrial support amino acid, a sensory agent configured to provide warming or tingling cues, a bioavailability enhancer, a phospholipid, selected vitamins and minerals, an acidulant system, and water. In certain embodiments, the dopamine precursor comprises N-acetyl L-tyrosine at about 100 to 700 milligrams per unit dose. The choline donor may comprise citicoline at about 100 to 400 milligrams per dose. A phospholipid such as phosphatidylserine may be present at about 50 to 300 milligrams per dose. Adaptogenic botanicals may include one or more of *Rhodiola rosea* extract at about 25 to 250 milligrams, *Panax ginseng* extract at about 50 to 350 milligrams, Bacopa monnieri extract at about 50 to 350 milligrams, and Lion's Mane extract at about 100 to 700 milligrams per dose. A vascular or mitochondrial support component may comprise L-citrulline at about 100 to 600 milligrams per dose. A bioavailability enhancer may comprise piperine at about 2 to 10 milligrams per dose. A sensory agent, warming, tingling, or flushing agent may comprise ginger $CO_2$ extract at about 3 to 20 milligrams per dose to provide perceivable warming or tingling within minutes of ingestion. Vitamins and minerals may include vitamin B6 at about 2 to 10 milligrams, vitamin B12 at about 25 to 200 micrograms, and magnesium glycinate providing about 10 to 80 milligrams elemental magnesium per dose. An acidulant system may include malic acid, optionally with limited citric acid, to adjust pH to about 3.0 to 3.5. The total solids of the finished liquid may be about 5.5 to 7.2 percent to balance mouthfeel and rapid gastric emptying. Flavor systems and optional non nutritive sweeteners may be selected to favor rapid palate clearance, for example within about sixty seconds after swallowing.

In certain coffee-congruent embodiments, the composition further includes a substantially oil-free flavor system configured to remain neutral with respect to a later coffee beverage. The flavor system may include roasted cacao nib water-soluble extracts having a fat content of less than about one percent by weight, coffee-cherry or cascara water extracts, and an oil-free vanilla flavor, optionally in combination with a ginger $CO_2$ extract that provides a defined gingerol content contributing a controlled warmth cue. Sub-ppm levels of oil-free fruit esters, such as ethyl 3-hydroxybutyrate and ethyl 2-methylbutyrate, may be employed to adjust perceived brightness without introducing a persistent aftertaste or interfering with the flavor of a subsequently consumed coffee beverage.

To preserve coffee compatibility and sensory neutrality, certain embodiments are substantially free of citrus peel oils and terpenes, for example with a combined level of limonene and citral from citrus peel sources at or below about 1.0 part per million. The compositions may also be substantially free of dairy or other fat-containing emulsions, such that total fat does not exceed about 0.05 percent by weight, and substantially free of quillaja, for example with quillaja content not greater than about 5 parts per million. Conversely, oil-free fruit esters may be present at combined levels up to about 2.0 parts per million to adjust aromatic brightness while maintaining coffee flavor neutrality.

Compositions may be prepared by charging a jacketed mixing vessel with potable water equal to about 80 to 90 percent of batch weight and beginning moderate agitation. Operators may add the acidulant system first and titrate to the target pH using a calibrated meter. Soluble amino acids such as L-citrulline and mineral sources such as magnesium glycinate may then be dissolved to reduce localized supersaturation later in the process. Citicoline and N-acetyl L-tyrosine may be added slowly to avoid clumping, with sifting through a 20 to 40 mesh screen when provided as powders. Adaptogenic extracts may be added as standardized powders or liquids; where flavor impact warrants, certain botanicals may be provided as microencapsulated particles that hydrate under agitation to moderate bitterness and astringency while maintaining dissolution. Phosphatidylserine may be dispersed under controlled shear or introduced as a pre-emulsion per supplier guidance. Piperine, ginger $CO_2$ extract, and other volatile or oleoresin materials may be added near the end of mixing to reduce volatilization or wall adsorption. The batch may then be brought to final weight with water, mixed an additional five to ten minutes to ensure homogeneity, and optionally filtered through a food-grade screen prior to filling.

The liquid may be filled as a cold-fill product into PET or glass containers sized to hold about 2.0 to 3.0 ounces per unit dose. Headspace may be purged with nitrogen, and closures may be torqued according to supplier specifications. The packaged product may undergo high-pressure processing or a low-temperature pasteurization profile to achieve microbial stability while moderating heat exposure for sensitive actives. Optional low-level carbonation at about 0.25 to 0.4 volumes of carbon dioxide may be dosed in-line to adjust mouthfeel and sensory trajectory without materially changing pH. Shelf life may be established through real-time and accelerated stability studies; for example, certain formulations may achieve about twelve months under refrigeration or about six months at ambient storage, subject to verification in the final commercial package.

In certain embodiments, microbial stability is achieved by high-pressure processing at pressures on the order of about 600 megapascals for a dwell time of about three minutes at a product temperature between about 4 and 8 degrees Celsius, thereby preserving the sensory arc and dissolved carbon dioxide levels. In alternative embodiments, the composition may be acidified to a pH at or below about 3.35 and preserved with potassium sorbate present at about 200 to 300 milligrams per liter, enabling ambient distribution without retort or hot-fill processing. The compositions may be cold-filled with a nitrogen headspace and configured to maintain dissolved oxygen at or below about 4 parts per million at pack, so as to support flavor stability and the desired sensory trajectory over shelf life.

In one packaging configuration, the unit-dose liquid composition is filled into a container sized to hold between about 2 and 3 ounces, formed from a material having a ultraviolet light transmission of not more than about ten percent at a wavelength of 450 nanometers. The container may be sealed with a closure that includes an induction seal and is applied at a torque between about 1.4 and 1.8 newton-meters, with a nitrogen headspace and an oxygen-scavenging component such that headspace oxygen at pack is at or below about one percent by volume.

Use instructions may direct a user to administer one unit dose about 2 to 45 minutes before consuming a caffeinated beverage. Certain routines may specify a window of about 2 to 25 minutes to provide perceivable effects to a majority of users prior to caffeine intake. A caffeinated beverage may then be consumed within about 10 to 30 minutes after administration. The sensory agent may provide an initial cue, such as tingling or warmth, followed by a transient heat or flush and a subsequent fade, which may help a user recognize timing without modifying the flavor of a later beverage.

Quality and performance characterization may include measuring pH at 20 to 25 degrees Celsius with a calibrated meter, verifying total solids by refractometry or gravimetry, and confirming content uniformity by batch sampling and appropriate analytical methods for representative actives. Palate clearance may be assessed using a timed sensory protocol in which trained panelists record the disappearance of perceivable aftertaste within about sixty seconds. Compatibility with brewed coffee or other caffeinated beverages consumed shortly after administration may be evaluated using a triangle sensory test at a defined significance level. Sensory timing may be recorded by panelists who log onset and resolution of warming or tingling and any transient heat or flush. Triangle difference testing may be conducted according to ISO 4120 methodology, and hedonic acceptability testing may follow ISO 4121 protocols. Dissolved carbon dioxide levels may be measured using standard beverage carbonation analyzers, with values recorded at the time of opening and at approximately ten seconds after ingestion for correlation with perceived exhale cues. Gingerol content in the ginger $CO_2$ extract or other ginger components may be quantified by ultra-high performance liquid chromatography with mass spectrometry or gas chromatography with mass spectrometry, with appropriate calibration and stated limits of detection and quantitation. Osmolality may be determined according to United States Pharmacopeia <785>. For purposes of this disclosure, "caffeine-free" indicates that no caffeine is intentionally added and that residual caffeine, if present, does not exceed about five milligrams per serving as measured by high-performance liquid chromatography.

Illustrative compositions may be formulated within the ranges described above. By way of example, a 2.5-ounce unit dose may include approximately: N-acetyl L-tyrosine 300 milligrams, citicoline 250 milligrams, phosphatidylserine 150 milligrams, L-citrulline 300 milligrams, ginger $CO_2$ extract 10 milligrams, piperine 5 milligrams, vitamin B6 5 milligrams, vitamin B12 100 micrograms, magnesium glycinate providing 40 milligrams elemental magnesium, malic acid sufficient to reach pH about 3.2 with limited citric acid if used, optional flavoring and non nutritive sweetener to reach total solids about 6.0 percent, and water to volume. The composition may be cold-filled into nitrogen-flushed 2.5-ounce containers and subjected to high-pressure processing, with optional carbonation at about 0.3 volumes.

For a standardized 2.5-ounce unit dose, corresponding to approximately 74 milliliters, certain embodiments are formulated as high-acid beverages having a pH in the range of about 3.1 to 3.6, more preferably about 3.2 to 3.4, a dissolved carbon dioxide level of about 0.15 to 0.25 volumes, and a dissolved oxygen level not greater than about 4 parts per million at the time of packaging. Osmolality may be maintained between about 600 and 900 milliosmoles per kilogram, such as less than about 800 milliosmoles per kilogram, to balance perceived intensity, mouthfeel, and gastrointestinal comfort. Sodium chloride in an amount of about 8 to 20 milligrams per 2.5-ounce unit dose may optionally be included as a taste modulator without contributing a functional electrolyte claim.

Alternative dosage formats may also be produced when desired. The compositions may be provided as ready-to-drink liquid shots having a unit dose between about 2.0 and 3.0 ounces, as powders in sachets or sticks configured for reconstitution to a unit-dose beverage between about 50 and 120 milliliters, as chewable or gummy dosage forms, as orally dissolvable films, and as concentrates intended for dilution. The pre-caffeine administration timing window of about 2 to 45 minutes and the sensory system described herein can be applied across these formats, with effervescence produced at pack for liquid embodiments or upon reconstitution for powder embodiments. In powder embodiments, reconstitution to the unit-dose beverage may provide a dissolved carbon dioxide level of at least about 0.5 volumes and a palate-clear endpoint within about sixty seconds after swallowing, thereby generating a perceived exhale cue analogous to that of a lightly carbonated liquid shot. Liquid embodiments at pack may be formulated to provide about 0.15 to 0.25 volumes of dissolved carbon dioxide, which yields at least about 0.05 volumes of carbon dioxide release within about ten seconds after ingestion.

Powder embodiments may be packaged in multi-layer, high-barrier sachets or stick packs exhibiting a moisture vapor transmission rate not greater than about 0.1 grams per square meter per day and an oxygen transmission rate not greater than about 1 cubic centimeter per square meter per day, optionally with nitrogen flushing and a desiccant in the secondary carton. Film embodiments may be packaged in foil-foil blister cards having an oxygen transmission rate not greater than about 0.1 cubic centimeters per square meter per day and configured for storage at relative humidity not exceeding about thirty percent.

FIG. 1 illustrates an administration timing timeline 100 for a single unit dose of a caffeine-free, ready-to-drink liquid composition. The timeline depicts representative events along a sequence following oral administration. At block 102, the user ingests the unit dose at time TO. At block 104, within about T+1-10 minutes, the user perceives a sensory cue, such as tingling or warmth, indicating initial onset following administration. At block 106, a T+2-25 minute interval defines a cognitive priming window during which perceptible effects (e.g., improved focus, clarity, motivation, or mood) may occur for a majority of users. At block 108, the user consumes a caffeinated beverage within about T+10-30 minutes after the unit dose, thereby coordinating subsequent caffeine intake with the priming window. At block 110, palate clearance occurs by about 60 seconds after swallow, indicating the composition does not substantially linger on the palate. Arrows indicate a forward progression of time; the illustrated intervals may partially overlap in practice, and the ranges include endpoints unless stated otherwise.

FIG. 2 depicts a composition schematic 202 identifying representative constituents of a caffeine-free, ready-to-drink liquid composition. The illustrated blocks denote components that may be included in a single unit dose; the arrangement is schematic and does not imply order of addition or relative proportion. The upper block identifies a sensory modulation system that provides perceivable cues following oral administration. Within this context, block 204 denotes a warming, tingling, or flushing agent configured to yield a prompt sensory signal after ingestion. Block 206 denotes a bioavailability enhancer comprising piperine, which may increase systemic exposure to one or more actives in the composition. Block 208 denotes a phospholipid comprising phosphatidylserine. Block 210 denotes vitamins comprising vitamin B6 and vitamin B12. Block 212 denotes a mineral comprising magnesium glycinate. lock 214 denotes an acidulant system comprising malic acid with citric acid limited so as to maintain coffee compatibility, thereby achieving the target pH while reducing flavor interference with a subsequently consumed caffeinated beverage. The components shown in FIG. 2 may be formulated within the ranges set forth in the claims; unlabeled excipients (e.g., water, flavors, and sweeteners) may also be present though not depicted.

FIG. 3 illustrates a pre-caffeine cognitive priming flowchart 300 that summarizes representative functional characteristics of a caffeine-free, ready-to-drink liquid composition. The depicted blocks indicate properties evaluated after oral administration; the sequence is schematic and does not limit order, overlap, or timing unless expressly stated. At block 302, the composition clears from the palate in sixty seconds or less, indicating minimal lingering aftertaste. At block 304, the composition produces at least three perceptible effects selected from improved focus, enhanced motivation, elevated mood, reduced stress, or increased mental clarity within about 2 to 25 minutes following administration. At block 306, the composition provides a multi-phase sensory arc comprising an initial tingling or warmth followed by a transient heat or flush. At block 308, the sequence includes induction of umami craving as part of the experiential profile. At block 310, the composition does not substantially alter the flavor or aroma of a caffeinated beverage consumed immediately thereafter (0-5 minutes) or within about 0-30 minutes thereafter, as validated by a triangle sensory test at a≤0.05. Arrows denote forward progression; ranges include endpoints unless indicated otherwise.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the art.

It will be appreciated by persons skilled in the art that the present embodiment is not limited to what has been particularly shown and described hereinabove. A variety of modifications and variations are possible considering the above teachings without departing from the following claims.

Instructions: the composition may be administered 2-45 minutes prior to a caffeinated beverage, with the beverage consumed immediately thereafter (0-5 minutes) or within about 0-30 minutes; triangle testing is performed at 0-5 minutes, 0-10 minutes, and 10-30 minutes per ISO 4120.

Flavor System (Oil-Free, Coffee-Congruent)

Flavor systems include cacao nib water-soluble extracts (non-alkalized; <1% fat), coffee-cherry (cascara) water extracts, and oil-free vanilla concentrates. Optional sub-ppm oil-free fruit esters (e.g., ethyl 3-hydroxybutyrate 0.5-1.0 ppm; ethyl 2-methylbutyrate≤0.5 ppm) may be used to provide brightness. Citrus peel oils/terpenes are excluded to protect coffee flavor neutrality.

Matrix Windows

Unless otherwise specified, beverages are high-acid (pH 3.1-3.6), preferably pH 3.2-3.4, with dissolved $CO_2$ 0.15-0.25 volumes at pack, dissolved oxygen≤4 ppm at pack, and osmolality 600-900 mOsm/kg (preferably <800). An optional taste modulator such as sodium chloride 5-30 mg per 90 mL may be included.

Preservation

Preservation can be achieved by high-pressure processing (~600 MPa for ~3 minutes at 4-8° C.) or by acidified ambient shelf using potassium sorbate 200-300 mg/L at pH≤3.35; in both cases the composition is cold-filled with nitrogen headspace. Retort and hot-fill are not preferred due to sensory and carbonation loss.

Methods Anchors

Triangle testing per ISO 4120; hedonic testing per ISO 4121; osmolality per USP <785>; dissolved $CO_2$ measured by an instrument such as Zahm & Nagel with readings recorded at TO and 10 seconds post-ingestion; gingerol quantified by UHPLC-MS or GC-MS (calibration $R^2$≥0.99; LOD/LOQ reported); caffeine-free defined as no added caffeine and ≤5 mg per serving by HPLC.

Negative Limits (Coffee-Neutral Moat)

The compositions are substantially free of citrus peel terpenes (e.g., limonene+citral≤1.0 ppm total), dairy/fat emulsions (total fat≤0.05% w/w), and quillaja saponins (≤5 ppm); oil-free fruit esters at ≤2.0 ppm total may be included to adjust brightness without materially affecting coffee flavor.

Powder/Film/Gummy Embodiments

The compositions may be provided as ready-to-drink liquid shots (2.0-3.0 oz), powders configured for reconstitution to 50-120 mL, chewable/gummy dosage forms, or orally dissolvable films. The pre-caffeine timing (2-45 min) and sensory system apply to these formats; liquids may provide $CO_2$ at pack; powders may provide $CO_2$≥0.5 volumes upon reconstitution. Packaging for powders may comprise high-barrier sachets (MVTR≤0.1 g/m$^2$/day; OTR≤1 cc/m$^2$/day; nitrogen flush; desiccant in carton) and films may be packed in foil-foil blisters (OTR≤0.1 cc/m$^2$/day; ≤30% RH storage).

I claim:

1. A caffeine-free liquid composition for pre-caffeine priming, formulated for oral administration in a unit dose of 50 to 120 mL and having a pH of 3.0-3.5, the composition comprising:

(a) a dopamine precursor comprising N-acetyl L-tyrosine;

(b) a choline donor comprising citicoline;

(c) an amino acid comprising L-citrulline;

(d) a phospholipid selected from phosphatidylserine, phosphatidylcholine, phosphatidylinositol, and combinations thereof;

(e) a bioavailability enhancer;

(f) vitamins comprising vitamin B6 and vitamin B12;

(g) a magnesium source;

(h) an acidulant system comprising malic acid with citric acid limited so as to maintain flavor compatibility; and (i) a masking/stability system comprising a cyclodextrin, a phospholipid, and an octenyl-succinic-anhydride modified starch;

wherein the composition optionally contains dissolved carbon dioxide.

2. The composition of claim 1, wherein aftertaste clears in ≤60 seconds as measured by a trained panel.

3. The composition of claim 1, wherein ingestion of a caffeinated coffee within about 0 to 30 minutes after administration of the composition is not substantially altered in flavor or aroma as validated by ISO 4120 triangle test.

4. The composition of claim 1, wherein dissolved carbon dioxide at pack is 0.15 to 0.25 volumes and osmolality is <800 mOsm/kg measured by United States Pharmacopeia <785> (USP <785>).

5. The composition of claim 1, wherein dissolved oxygen at pack is ≤4 ppm.

6. The composition of claim 1, wherein the composition is substantially free of citrus peel terpenes comprising limonene and citral at a combined concentration≤1.0 ppm.

7. The composition of claim 1, wherein total fat is ≤0.05% (w/w) and quillaja saponins are ≤5 ppm.

8. The composition of claim 1, wherein oil-free fruit esters are present at ≤2.0 ppm total.

9. The composition of claim 1, wherein the masking/stability system comprises β-cyclodextrin 0.25 to 0.45 g per 90 mL, a phospholipid 0.10 to 0.25 g per 90 mL, and octenyl succinic anhydride-modified starch 0.08 to 0.16 g per 90 mL.

10. The composition of claim 1, wherein the composition is caffeine-free with no added caffeine≤5 mg per serving measured by high-performance liquid chromatography (HPLC).

11. The composition of claim 1, further comprising sodium chloride 5 mg per 90 mL to 30 mg per 90 mL as a taste modulator.

12. The composition of claim 1, wherein the bioavailability enhancer comprises piperine.

13. A sensory system for pre-caffeine priming comprising a unit-dose composition according to claim 1 and instructions for pre-caffeine administration, wherein ingestion produces a quantified sensory sequence comprising: (i) an exhale cue defined by dissolved CO2 release≥0.05 volumes within 10 seconds post-ingestion; (ii) a warmth cue defined by gingerol-equivalent 0.5 to 1.5 ppm; and (iii) a clean fade of residual flavor intensity≤$\frac{1}{10}$ at ≤60 seconds as measured by trained panelists.

14. The system of claim 13, wherein dissolved $CO_2$ at pack is 0.15 to 0.25 volumes and pH is 3.2-3.4.

15. The system of claim 13, wherein the instructions direct consumption of a caffeinated coffee beverage immediately thereafter or within about 0 to 30 minutes of administration.

16. An article of manufacture comprising a container having a capacity of 50 to 120 mL containing the composition of claim 1, the container comprising amber polyethylene terephthalate (amber PET) or glass, wherein the container has a UV transmittance≤10% at 450 nm, an oxygen-scavenger and induction-seal liner, headspace nitrogen, a closure torqued 1.4 to 1.8 N·m, and headspace $O_2$≤1.0% v/v at sealing.

17. The article of claim 16, wherein the article comprises a unit-dose powder packaged in a multi-layer high-barrier sachet having a moisture vapor transmission rate≤0.1 g/m²/day and an oxygen transmission rate≤1 cc/m²/day and further comprising nitrogen flushing and a desiccant in a secondary carton.

18. The article of claim 16, wherein the article comprises an orally dissolvable film packaged in a foil-foil blister card having an oxygen transmission rate≤0.1 cc/m²/day and configured for storage at relative humidity≤30%.

* * * * *